US012690816B2

(12) United States Patent
Ohayon

(10) Patent No.: US 12,690,816 B2
(45) Date of Patent: Jul. 28, 2026

(54) APPLICATION BASED DETERMINATION OF VITAL SIGNS AND A PHYSIOLOGICAL STATE WITH APPLICATION BASED ACTION INITIATION

(71) Applicant: BRIGHTERMD LLC, Plano, TX (US)

(72) Inventor: Jesse Ohayon, Plano, TX (US)

( * ) Notice: Subject to any disclaimer, the term of this patent is extended or adjusted under 35 U.S.C. 154(b) by 982 days.

(21) Appl. No.: 17/933,620

(22) Filed: Sep. 20, 2022

(65) Prior Publication Data

US 2024/0090845 A1    Mar. 21, 2024

(51) Int. Cl.
| | |
|---|---|
| *A61B 5/00* | (2006.01) |
| *G06F 18/23213* | (2023.01) |
| *G06N 3/02* | (2006.01) |
| *G06N 20/00* | (2019.01) |

(52) U.S. Cl.
CPC .......... *A61B 5/7264* (2013.01); *A61B 5/7289* (2013.01); *G06F 18/23213* (2023.01); *G06N 3/02* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 8,684,922 | B2 | 4/2014 | Tran |
| 10,610,111 | B1 | 4/2020 | Tran |
| 10,694,988 | B2 | 6/2020 | Lee et al. |
| 11,096,581 | B2 | 8/2021 | Hickle et al. |
| 11,308,618 | B2 | 4/2022 | Connor |
| 11,342,076 | B1 | 5/2022 | Jagirdar et al. |
| 2008/0166992 | A1 | 7/2008 | Ricordi et al. |
| 2009/0088607 | A1 | 4/2009 | Muraca |
| 2015/0065826 | A1* | 3/2015 | Mulligan ............. A61B 5/7275 |
| | | | 600/323 |
| 2016/0086500 | A1* | 3/2016 | Kaleal, III ............. G16H 40/63 |
| | | | 434/257 |
| 2017/0011192 | A1 | 1/2017 | Arshad et al. |
| 2019/0046099 | A1* | 2/2019 | Lee ........................ A61B 5/024 |
| 2020/0029837 | A1 | 1/2020 | Joudi |
| 2020/0315511 | A1* | 10/2020 | Lee ........................ A61B 5/024 |
| 2021/0045640 | A1* | 2/2021 | Poltorak ............. A61B 5/0022 |
| 2021/0225516 | A1* | 7/2021 | Liu ........................ G16H 50/30 |
| 2021/0407669 | A1 | 12/2021 | Fish et al. |
| 2022/0005191 | A1* | 1/2022 | Connor ................. G06T 7/0012 |
| 2022/0138941 | A1 | 5/2022 | Yen et al. |
| 2022/0142590 | A1 | 5/2022 | Modai et al. |

FOREIGN PATENT DOCUMENTS

| | | |
|---|---|---|
| GB | 2586433 A | 2/2021 |
| KR | 1020220019340 A | 2/2022 |
| WO | 2021055427 A1 | 3/2021 |

* cited by examiner

*Primary Examiner* — Gabriel I Garcia
(74) *Attorney, Agent, or Firm* — Scheef & Stone, L.L.P.; Keith C. Rawlins, Esq.

(57) ABSTRACT

A method, application program, smart device, and computer system may capture images of a body part of a patient, determine one or more vital signs of the patient by image processing optionally assisted by a machine learning model, determine a physiological state for one or more of the vital signs with a computational model generated by another machine learning model, and initiate a communication with a medical professional's communication device based on the physiological state being outside a threshold range.

20 Claims, 4 Drawing Sheets

2000

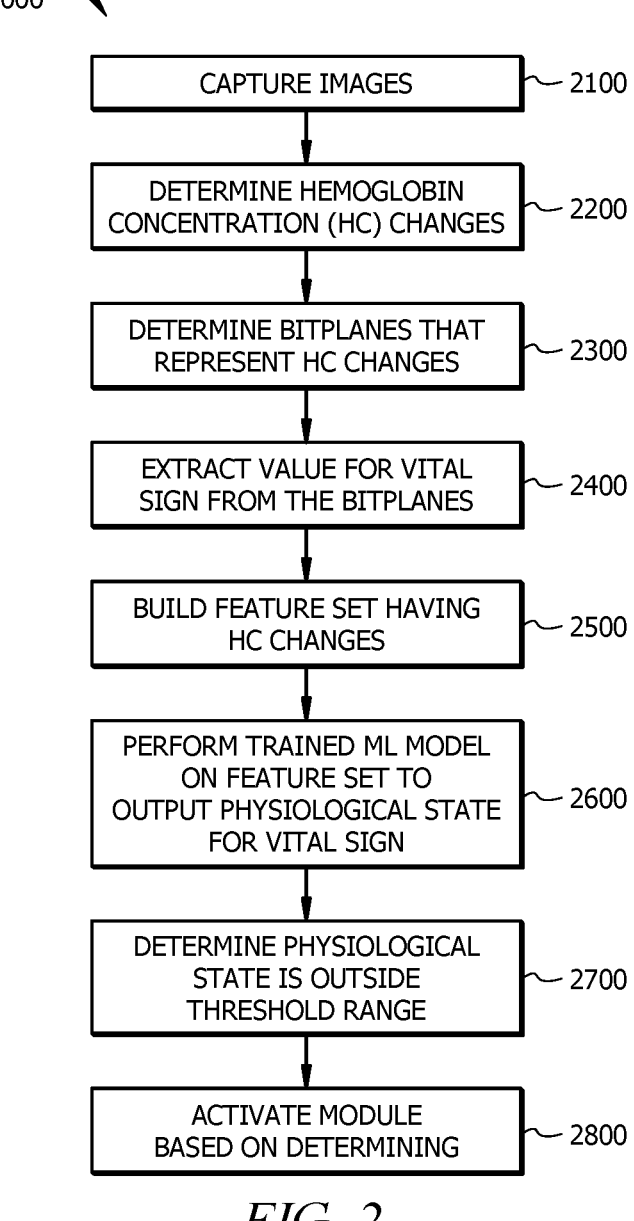

CAPTURE IMAGES — 2100

DETERMINE HEMOGLOBIN
CONCENTRATION (HC) CHANGES — 2200

DETERMINE BITPLANES THAT
REPRESENT HC CHANGES — 2300

EXTRACT VALUE FOR VITAL
SIGN FROM THE BITPLANES — 2400

BUILD FEATURE SET HAVING
HC CHANGES — 2500

PERFORM TRAINED ML MODEL
ON FEATURE SET TO
OUTPUT PHYSIOLOGICAL STATE
FOR VITAL SIGN — 2600

DETERMINE PHYSIOLOGICAL
STATE IS OUTSIDE
THRESHOLD RANGE — 2700

ACTIVATE MODULE
BASED ON DETERMINING — 2800

RECEIVE DATA FROM SMART DEVICE(S) —— 3100

DETERMINE HC CHANGES —— 3200

DETERMINE BITPLANES THAT REPRESENT HC CHANGES —— 3300

EXTRACT SPATIAL-TEMPRAL FEATURES TO CREATE TRAINING FEATURE SET —— 3400

PERFORM ML MODEL ON FEATURE SET TO GENERATE COMPUTATIONAL MODEL —— 3500

APPLICATION BASED DETERMINATION OF VITAL SIGNS AND A PHYSIOLOGICAL STATE WITH APPLICATION BASED ACTION INITIATION

FIELD OF THE DISCLOSURE

The present disclosure generally relates to application based determination of vital signs and a physiological state of a patient in combination with application based action initiation.

BACKGROUND

Remote medical care is primarily conducted by a medical professional viewing images of the patient that are streamed during a real-time two-way streaming video session. The resolution of the video quality can vary depending on network operation and network connections, and even for high quality data connections, the medical professional's observation of the patient during the video session can be challenging compared to an in-person consultation. For example, the medial professional cannot use his/her stethoscope to observe heart rate or breathing patterns of a patient during a streaming video session and cannot shine a light into the patient's eye to observe pupil reaction.

Moreover, the medical professional is likely to gather vital signs information by asking the patient questions during the video session and/or by having the patient read vital signs data from a self-administered device such as a thermometer or a wearable device such as a smart watch. The information gathering takes time and is a part of the streaming video session that occurs before the medical professional is able to advise about the patient's medical condition. While wearable devices might have the ability to report data such as heart rate of the patient to a data account of the patient (e.g., iCloud for the Apple Watch), the data is not readily available to the medical professional during the streaming video session.

Remote-patient systems exist for monitoring equipment status or a patient's status, such as for monitoring a status of a rehabilitation device or monitoring heart rate, where the device or monitor can be configured to send a signal to a remote computer upon the occurrence of an event that is outside of a threshold range for a signal indicating the event. The signal can be used to trigger an action, such as to prompt a person at a call center to call for medical attention. However, these remote-patient systems are designed for reactive action. That is, these remote-patient systems are used after an equipment or health event involving the patient has occurred.

SUMMARY

In some aspects, the techniques described herein relate to a method including: capturing, by camera of a smart device, a plurality of images of a body part of a patient; determining, by the smart device, a plurality of hemoglobin concentration (HC) changes based on the plurality of images; determining, by the smart device, a set of bitplanes of the plurality of images that represent the plurality of hemoglobin concentration (HC) changes of the patient; extracting, by the smart device, a value for a vital sign from the plurality of HC changes; building, by the smart device, a feature set including the plurality of HC changes; performing, by the smart device, a trained machine learning model including a computational model on the feature set to obtain an output data set including a physiological state for the vital sign; determining, by the smart device, the physiological state is outside of a threshold range; and activating, by the smart device, a call module or a video streaming module running on the smart device based on determining the physiological state is outside of the threshold range.

In some aspects, the techniques described herein relate to a computer system including a smart device, wherein the smart device is configured to: capture, by camera of the smart device, a plurality of images of a body part of a patient; determine, by an application program running on the smart device, a plurality of hemoglobin concentration (HC) changes based on the plurality of images; determine, by the application program, a set of bitplanes of the plurality of images that represent the plurality of hemoglobin concentration (HC) changes of the patient; extract, by the application program, a value for a vital sign from the plurality of HC changes; build, by the application program, a feature set including the plurality of HC changes; perform, by the application program, a trained machine learning model including a computational model on the feature set to obtain an output data set including a physiological state for the vital sign; determine, by the application program, the physiological state is outside of a threshold range; and activate, by the application program, a call module running on the smart device or a video streaming module of the application program based on determining the physiological state is outside of the threshold range.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which:

FIG. 2 illustrates a flow diagram of a method for determining one or more vital signs and one or more physiological states associated with the one or more vital signs.

DETAILED DESCRIPTION

Figure 1:
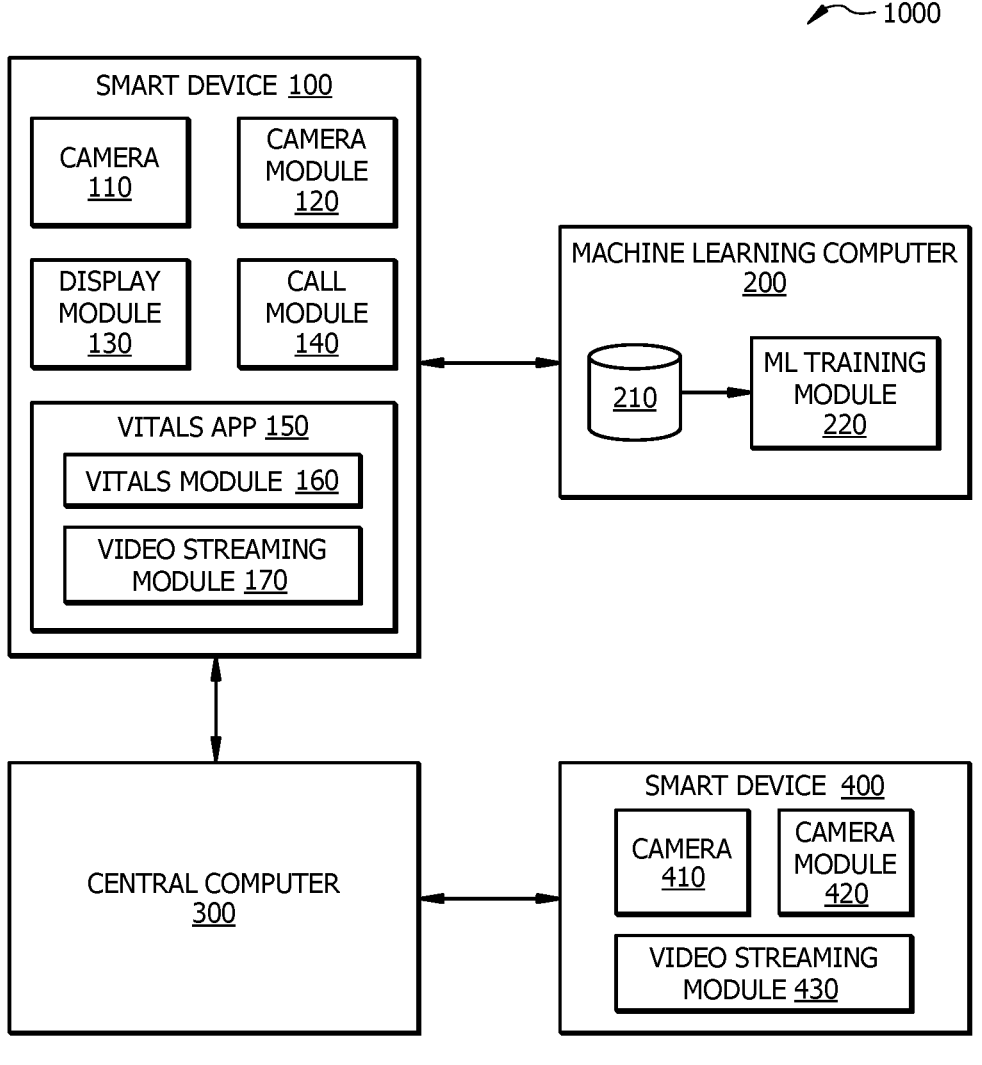
FIG. 1 illustrates a schematic diagram of a computer system for determining one or more vital signs of a patient and a physiological state of a patient with a smart device and for initiating an action in response to the determined physiological state.

"Application program" or "application" or "app" as used herein refers to instructions stored on and/or running on a patient computer device, which when executed by a processor of the patient computer device, cause the patient computer device to perform the function(s) of the application disclosed herein.

"Telehealth" or "telemedicine" as used herein refers to medical care conducted between a medical professional and a patient, virtually between a computer device of the medical professional and a computer device of the patient.

"Vital sign" or "vital signs" as used herein can include, but are not limited to, heart rate, respiratory rate, blood pressure, blood oxygen index, temperature, or combinations thereof, of a patient.

"Physiological state" as used herein refers to a status of a vital sign or combination of vital signs. For example, a physiological state of a patient's vital sign that is determined by a technique disclosed herein can be normal, elevated, or severe. Additionally or alternatively, the physiological state of the patient's vital sign that is determined by a technique disclosed herein can be relative to a risk of a medical event, e.g., low risk, normal risk, high risk relative to having a heart attack.

Disclosed herein are methods, application program, smart device, and computer system that may capture images of a body part of a patient, determine one or more vital signs of the patient by image processing optionally assisted by a machine learning model, determine a physiological state for one or more of the vital signs with a computational model generated by another machine learning model, and initiate a communication with a medical professional's communication device based on the physiological state being outside a threshold range.

In aspects, the methods, application program, smart device, and computer system can determine one or more vital signs of a patient and a physiological state of the patient, determine whether the physiological state is outside a threshold range, and initiate an action such as a phone call or a streaming video session based on the physiological state being outside the threshold range. The physiological state can be determined by a smart device running an application program disclosed herein because 1) images of a body part of a patient can be captured by the camera of the smart device, 2) the images can contain the color signature of hemoglobin concentration (HC), 3) the smart device can be programed to isolate HC changes from the images captured by the camera the smart device, and 4) the HC changes can be correlated to human physiological states. Particularly, a camera of a smart device can capture the re-emission of light from the skin of a patient's body part using the camera of the smart device. That is, light from a light source can enter the epidermis layer of the skin of the patient and deflect or reflect from the epidermis and/or one or more layer of skin below the epidermis (e.g., papillary dermis or reticular dermis). The images captured by the camera of the smart device can contain the color signature of hemoglobin concentration in the deflected or reflected light.

FIG. 1 illustrates a schematic diagram of a computer system 1000 for determining one or more vital signs of a patient and a physiological state of a patient with a smart device 100 and for initiating an action in response to the determined physiological state. The computer system 1000 can include the smart device 100 (a smart device of a patient), a machine learning computer 200, a central computer 300, and a smart device 400 (a smart device of a medical professional). While one patient smart device 100 is illustrated in FIG. 1 as being networked with the machine learning computer 200 and the central computer 300, the disclosure contemplates that a plurality of patient smart devices can be networked with the machine learning computer 200 and with the central computer 300, where each of the patient smart devices contains the hardware and software functionality described for smart device 100 herein. Similarly, while one medical professional smart device 400 is illustrated in FIG. 1 as being networked with the central computer 300, the disclosure contemplates that a plurality of medical professional smart devices can be networked with the central computer 300, where each of the smart devices contains the hardware and software functionality described for smart device 400 herein.

The smart device 100 can be embodied as a smart phone, tablet, laptop, PC, or other computer device. Commercially available smart devices include Apple, Samsung, Google, and Huawei. The smart device 100 can have a camera 110, a camera module 120, a display module 130, a call module 140, and one or more application programs that include the application program 150 of this disclosure. In aspects, the smart device 100 can include chipsets that have a dedicated machine learning interference chip, such as those offered by Samsung, Qualcomm, ARM, Nvidia, or Huawei.

The application program 150 can have a vitals module 160 that is configured to determine one or more vital signs of a patient and a physiological state of a user of the smart device 100 and a video streaming module 170 that is configured to initiate an action based on a physiological state that is determined by the vitals module 160, as described in more detail herein.

The vitals module 160 of the application program 150 of the smart device 100 is configured to receive a first trained computational model from the machine learning computer 200 and to run the first trained computational model in the vitals module 160 to perform functionality described herein. In aspects, the vitals module 160 can periodically receive an updated trained computational model from the machine learning computer 200, replace the first trained computational model with the updated trained computational model, and run the updated trained computational model in the vitals module 160 to perform functionality described herein.

The video streaming module 170 is configured to initiate and conduct a streaming video session after the vitals module 160 determines a physiological state is outside of a threshold range. Communications between the vitals module 160 and the video streaming module 170 are described in more detail herein.

The machine learning computer 200 can include one or more processors, memory, networking cards or interfaces, and other equipment for performing the method and functionality disclosed herein. In embodiments, the machine learning computer 200 can be include multiple computers, located in a brick-and-mortar location, local to the administrator of the machine learning computer 200, in the cloud, or a combination thereof. In FIG. 1, the machine learning computer 200 has a datastore that is configured to store training data. The machine learning computer 200 also has a machine learning (ML) training module 220 that is configured to generate training data sets for training a computational model. The computational model is periodically trained with updated training data sets to generate the updated trained computational model that can be sent by the machine learning computer 200 to the vitals module 160 of the application program 150 running on the smart device 100.

The central computer 300 can include one or more processors, memory, networking cards or interfaces, and other equipment for performing the method and functionality disclosed herein. The central computer 300 is configured to administer two-way streaming video sessions between the smart device 100 and a smart device 400 of a medical professional that has a camera and a software module for streaming video streaming. can utilize video streaming technology and architecture to provide the real-time video session 203. In embodiments, the computer system 1000 can utilize multimedia routing or decentralized video conferencing by which the central computer 300 can match the smart device 100 with the smart device 400, and the video streaming module 170 of the smart device 100 can connect directly with the video streaming module 430 of the smart device 400 via one or more networks disclosed herein, for a live real-time video session between the smart devices 100 and 400. Alternatively, central computer 300 can utilize a multipoint control unit (MCU) by which the MCU can receive and present the video streams from and to the video streaming module 170 of the smart device 100 and from and to the video streaming module 430 of the smart device 400.

In embodiments, the central computer 300 can include multiple computers, located in a brick-and-mortar location, local to the administrator of the central computer 300, in the cloud, or a combination thereof. In embodiments, the central computer 300 can include a distributed computer architecture, such that hardware is geographically distributed to one or more smart devices 100 with the hardware that is geographically closest to the smart device 100. In some aspects, the central computer 300 can include computers embodied as servers that are scalable in the cloud, such as those available from Amazon Web Services.

The smart device 400 can be embodied as a smart phone, tablet, laptop, PC, or other computer device. The smart device 400 can have a camera 410, a camera module 420, and a video streaming module 430. The video streaming module 430 interacts with central computer 300 and with the camera module 420 when conducting a video session with the central computer 300. The camera module 420 controls the camera 410 of the smart device 400.

The smart device 100 is networked with the machine learning computer 200 and with the central computer 300.

The smart device 100 and the machine learning computer 200 can be networked via any wired internet connection, wireless internet connection, local area network (LAN), wired intranet connection, wireless intranet connection, or combinations thereof. The networks used for communication between the smart device 100 and the machine learning computer 200 can include a Global System for Mobile Communications (GSM), Code-division multiple access (CDMA), General Packet Radio Service (GPRS), Evolution-Data Optimized (EV-DO), Enhanced Data Rates for GSM Evolution (EDGE), Universal Mobile Telecommunications System (UMTS), etc.

The smart device 100 and the central computer 300 can be networked via any wired internet connection, wireless internet connection, local area network (LAN), wired intranet connection, wireless intranet connection, or combinations thereof. The networks used for communication between the smart device 100 and the central computer 300 can include a Global System for Mobile Communications (GSM), Code-division multiple access (CDMA), General Packet Radio Service (GPRS), Evolution-Data Optimized (EV-DO), Enhanced Data Rates for GSM Evolution (EDGE), Universal Mobile Telecommunications System (UMTS), etc.

The smart device 400 is networked with the central computer 300. The smart device 400 and the central computer 300 can be networked via any wired internet connection, wireless internet connection, local area network (LAN), wired intranet connection, wireless intranet connection, or combinations thereof. The networks used for communication between the smart device 400 and the central computer 300 can include a Global System for Mobile Communications (GSM), Code-division multiple access (CDMA), General Packet Radio Service (GPRS), Evolution-Data Optimized (EV-DO), Enhanced Data Rates for GSM Evolution (EDGE), Universal Mobile Telecommunications System (UMTS), etc.

FIG. 2 illustrates a method 2000 for determining one or more vital signs and one or more physiological states associated with the one or more vital signs. The method 2000 is described with reference to components of the computer system 1000 in FIG. 1. The steps of the method 2000 are generally performed by the smart device 100.

In step 2100, the method 2000 includes capturing, by the camera 110 of the smart device 100, a plurality of images of a body part of a patient. The camera module 120 of the smart device 100 can control the camera 110 to capture the plurality of images. The user of the smart device 100 (e.g., the patient) can initiate image capture by instructing the application program 150 to engage with the camera module 120 for image capture (e.g., via a virtual button displayed on the screen of the smart device 100 by the application program 150). The camera module 120 can be configured to cause the camera 110 to capture images at 1, 2, 3, 4, 5, 6, 7, 8, 9, 10, 20, 30, 40, or 50 frames per second, for example. The camera module 120 can be configured to cause the camera 110 to capture images for a period of time, e.g., 5, 10, 15, 20, 25, or 30 seconds; such that changes in hemoglobin concentrations can be determined from the images. The camera module 120 can be configured to construct a file containing a plurality of photo images (e.g., JPEG, PNG formats) or a video file (e.g., MP4, etc.) and send the file to the application program 150. The application program 150 can receive the file from the camera module 120 of the smart device 100.

In step 2200, the method 2000 includes determining, by the smart device 100, a plurality of hemoglobin concentration (HC) changes based on the plurality of images. The images captured by the camera of the smart device can contain the color signature of hemoglobin concentration in the deflected or reflected light. The plurality of HC changes can be determined using the color signatures of the HCs in the images.

In step 2300, the method 2000 includes determining, by the smart device 100, a set of bitplanes of the plurality of images that represent the plurality of hemoglobin concentration (HC) changes of the patient. In aspects, the set of bitplanes has a high signal to noise ratio (SNR). In aspects, a set of bitplanes having a high SNR is a set of bitplanes that optimizes or maximizes signal differentiation between different physiological states under the epidermis of the body part of the patient. In aspects, the vitals module 160 can include a machine learning model to determine the set of bitplanes having a red-green-blue (RGB) pixel bit-combination that maximizes the SNR. An example of a suitable machine learning model can be a K-means clustering model or a Long Short Term Memory (LSTM) neural network model that can obtain an accuracy of signal differentiation and that can determine which bitplane(s) have the highest SNR. The vitals module 160 can be configured to feed the output results of the machine learning model back as input into the machine learning model until two successive machine learning output results have values that are within a tolerance, such as +/−5, 4, 3, 2, or 1%, of one another. In aspects, ML model can be performed on only a portion of the total amount of data (e.g., 70%, 80%, 90% of the bitplanes data), and the vitals module 160 can use the remaining bitplanes data to validate the output of the ML model. In additional aspects, the ML model in step 2300 can be a trained ML model that is trained (e.g., by the machine learning computer 200 or by the application program 150) using a training set of images comprising the plurality of images from a training set of patients, EKG data from the training set of patients, pneumatic respiration data from the training set of patients, blood pressure data from the training set of patients, laser Doppler data from the training set of patients, oximeter data from the training set of patients, or combinations thereof.

In step 2400, the method 2000 includes extracting, by the smart device 100, a value for a vital sign from the bitplanes. An empirically-based HC isolation procedure can be performed on the HC changes, and the set of bitplanes that provides the highest SNR for a vital sign can be determined from the HC changes. The vital sign values can be extracted from the bitplanes. For example, the vital signs of heart rate, respiratory rate, blood pressure, and blood oxygenation index can be extracted by analyzing bitplanes of the plurality of images to determine and isolate a set of the bitplanes that most accurately correlate with EKG, pneumatic respiration, blood pressure, and the blood oxygenation machine data. The extracted vital sign value(s) can be displayed on the smart device 100 (e.g., via the report).

In step 2500, the method 2000 includes building, by the smart device 100, a feature set comprising the plurality of HC changes. In aspects, the feature set can also include stress level ratio(s) for value(s) of the vital sign. For example, one or more digital signal transformations (e.g. Fourier transformations) can be performed on the value of the vital and to obtain a stress level index. By comparing the stress level index against a normative stress index distribution profile that is included with the application program 150, a comparative stress ratio can be determined for the patient.

In step 2600, the method 2000 includes performing, by the smart device 100, a trained machine learning (ML) model on the feature set to obtain an output data set comprising a physiological state for the vital sign. In aspects, the trained ML model performed in step 2600 of the method 2000 is not the same model that may optionally be utilized in step 2300 of the method 2000. In aspects, the trained ML model can classify the HC changes as corresponding to a physiological state of the vital sign (or a combination of vital signs) of the patient.

In aspects of this disclosure, the trained ML model that is run on the application program 150 of the smart device 100 is received from the machine learning computer 200. As such, the trained ML model is a computational model that processes a feature set to obtain an output data set. The trained ML model running on the smart device 100 is not continuously updated by the smart device 100. Instead, in these aspects, the machine learning computer 200 continuously or periodically trains the computational model to produce an updated trained ML model (e.g., an updated computational model), and the application program 150 is configured to receive the updated trained ML model from the machine learning computer 200. The updated trained ML model is a later version of the earlier version of the computational model, that can be performed on another feature set to obtain another output data set. The machine learning computer 200 can send or propagate an updated trained ML model to the application program 150 of the smart device 100 periodically, such as daily, weekly, monthly, quarterly, semi-annually, or annually.

In alternative aspects of this disclosure, the smart device 100 can be equipment with chipsets configured for machine learning interference processing on the smart device 100 itself, e.g., an Ethnos model of chipsets commercially available from ARM. In such aspects, the vitals module 160 can use output data sets of the trained ML model to continuously or periodically train the trained ML model running on the vitals module 160 in order to update the trained ML model.

In step 2700, the method 2000 includes determining, by the smart device 100, the physiological state is outside of a threshold range. A threshold range can be that physiological state is severe, for example. In aspects, a physiological state for each vital sign can be determined, and as such, a plurality of physiological states are determined where a first physiological state corresponds to a first vital sign, a second physiological state corresponds to a second vital sign, and so on. In aspects, a comprehensive physiological state can correspond to a combination of vital signs.

In step 2800, the method 2000 includes activating, by the smart device 100, a call module 140 or a video streaming module 170 running on the smart device 100 based on determining the physiological state is outside of the threshold range. For a determined physiological state that is outside the threshold range, the vitals module 160 (which performs steps 2100 to 2700) can activate the video streaming module 170 or the call module 140.

The call module 140 can be any call module of a smart device 100, such as a standard call module that is pre-programmed on an iPhone or Samsung Galaxy mobile phone. The video streaming module 170 can be part of the application program 150. Thus, installation of the application program 150 can install the video streaming module 170 on the smart device 100, while the smart device 100 can be pre-equipped (pre-relative to the time of installation of the application program 150) with manufacturer-installed call module 140. In these aspects, the vitals module 160 that is installed as part of the application program 150 can communication with the manufacturer-installed call module 140 or the video streaming module 170.

In aspects where the call module 140 is activated, the vitals module 160 can send a phone number to the call module 140, and the call module 140 can utilize hardware and software on the smart device 100 to make a call over a cellular or internet network, for example. The phone number can be a number for a medical professional or a hospital, for example. The vitals module 160 can determine the proper phone number to send to the call module 140 in various manners. In some aspects, the vitals module 160 can include a mapping file that maps the physiological state of vital signs with phone numbers of medical professional contracted with the provider of the application program 150. For example, the physiological state for heart rate can be mapped to a phone number of a medical professional that is a heart specialist. The vitals module 160 can be configured to use the mapping file to match the physiological state or combination of physiological states that is/are outside the threshold range with the phone number of the medical professional associated with the vital sign(s) associated with the physiological state or combination of physiological states that are outside the threshold range. In other aspects, the vitals module 160 can be configured to receive input phone number from the patient via a medical professional input screen that can be displayed by display module 130 on the smart device 100. The vitals module 160 can be configured to retrieve the input phone number from the input file for the physiological state or combination of physiological states that is/are outside the threshold range. In other aspects, the vitals module 160 can send a message to the central computer 300, where the message contains information that the physiological state or combination of physiological states that is/are outside the threshold range. The central computer 300 can then determine the proper phone number (e.g., based on the physiological state or combination of physiological states that is/are outside the threshold range) of a medical professional contracted with the manufacturer of the application program 150 (and optionally the central computer 300). The central computer 300 can use a similar mapping file and matching technique as described for the vitals module 160. After determining the proper phone number, the central computer 300 can send a message to the vitals module 160 containing the proper phone number, and the vitals module 160 can interact with the call module 140 to call the proper phone number that is received from the central computer 300.

In aspects where the video streaming module 170 is activated, the video streaming module 170 can be configured to contact the central computer 300 with a request to initiate a two-way streaming video session. The video streaming module 170 can interact with the central computer 300 to establish the two-way streaming video session with the smart device 400 of a medical professional according to any technique known in the art with the aid of this disclosure.

Before initiating a streaming video session, the video streaming module 170 can determine the proper smart device 400 of a proper medical professional for the video streaming session in various manners. In some aspects, the video streaming module 170 can include a mapping file that maps the physiological state of vital signs with the IP addresses of smart device of medical professional contracted with the provider of the application program 150. For example, physiological state for heart rate can be mapped to the IP address of a smart device of a medical professional that is a heart specialist. The video streaming module 170 can be configured to use the mapping file to match the physiological state or combination of physiological states that is/are outside the threshold range with the IP address of the smart device of the medical professional associated with the vital sign(s) associated with the physiological state or combination of physiological states that are outside the threshold range. The video streaming module 170 can then send a message to the central computer 300 to initiate a video session with the mapped smart device of the proper medical professional. In other aspects, the vitals module 160 can be configured to receive input data from the patient via a medical professional input screen that can be displayed by display module 130 on the smart device 100. The vitals module 160 can store the input data for retrieval by the video streaming module 170. The video streaming module 170 can be configured to retrieve the input data from the input file for the physiological state or combination of physiological states that is/are outside the threshold range. The video streaming module 170 can then send a message to the central computer 300 to initiate a video session with the proper medical professional (the central computer 300 determining the IP address for the smart device of the proper medical professional). In other aspects, the video streaming module 170 can send a message to the central computer 300, where the message contains the request to initiate the two-way streaming video session and information that the physiological state or combination of physiological states that is/are outside the threshold range. The central computer 300 can then determine the IP address of the smart device of a proper medical profession (e.g., based on the physiological state or combination of physiological states that is/are outside the threshold range) contracted with the manufacturer of the application program 150 (and optionally the central computer 300). The central computer 300 can use a similar mapping file and matching technique as described for the video streaming module 170. After determining the proper IP address for the smart device (e.g., smart device 400), the central computer 300 can contact the smart device (e.g., smart device 400), and interact with the smart device 100 of the patient and the smart device 400 of the medical professional to establish the two-way video streaming session between the smart device 100 of the patient and the smart device 400 of the medical professional.

In aspects, the vitals module 160 can activate the call module 140 or the video streaming module 170 automatically without user/patient input between steps 270 and 280 of the method. Alternatively, the vitals module 160 can prompt, via a screen of the smart device 100, the user/patient for input (e.g., a virtual button) which is received prior to activating the call module 140 or the video streaming module 170.

Figure 3:
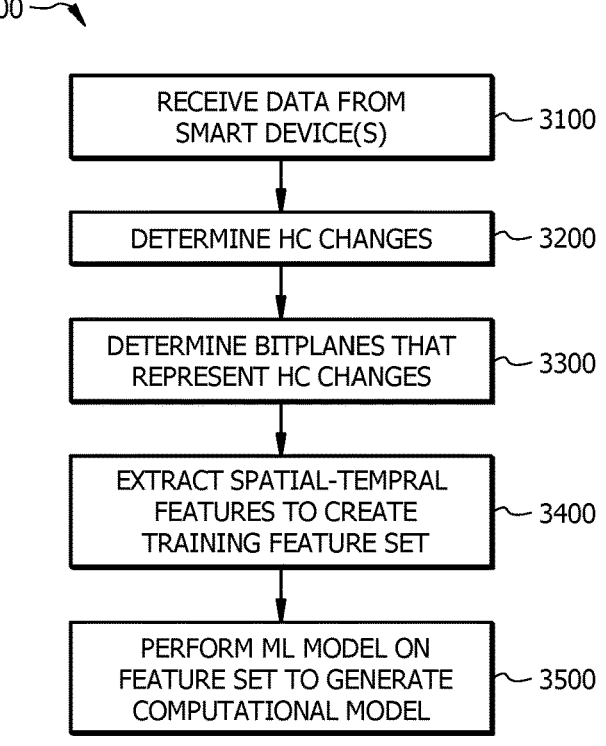
FIG. 3 illustrates a flow diagram of a method for training a machine learning (ML) model that is used as the computational model in the smart device.

FIG. 3 illustrates a flow diagram of a method 3000 for training a machine learning (ML) model that is used as the computational model in the vitals module 160 of the application program 150 running on the smart device 100. The method 3000 is described with reference to the components of the computer system 1000, and particularly with reference to the method 3000 being performed by the ML training module 220 of the machine learning computer 200. Alternative aspects contemplate that the method 3000 can be performed by the vitals module 160 or other module on the application program 150 running on the smart device 100, for example, in aspects where the smart device 100 has a dedicated machine learning interference chipset and memory storage capacity for training data sets.

In step 3100, the method 3000 includes receiving data, by the machine learning computer 200. In aspects, the data can be received from one or more smart devices (e.g., including smart device 100). The data received from any smart device can include any of the data received and generated by the application program 150 and similar application programs on other smart devices. For example, the data received by the machine learning computer 200 can include a file containing a plurality of images from a single scan run on the application program 150 of the smart device 100, several files each containing a plurality of images from several scans run on the application program 150 of the smart device 100, values of HC changes, determined bitplanes for a plurality of images, output results from the machine learning model that is run on the vitals module 160, one or more files containing images, HC changes, bitplanes, output results, or combinations thereof from any number of smart devices that similarly have the application program 150 running thereon.

In additional aspects of step 3100, the data can additionally be received from other data sources. For example, the machine learning computer 200 can receive and store training data from any source. The training data can include images (e.g., files of a sequence of still images or files of video images) of training patients that were exposed to stimuli known to elicit specific physiological states (e.g., the International Affective Picture System). Responses may be grouped in a manner that can be reported and communicated as a physiological state of one or a combination of vital signs (e.g., normal, elevated, and severe; or low stress, moderate stress, and high stress; or low pain, moderate pain, and high pain). In aspects, the training data set containing data from patients having groups of different skin types. The training data can include images (e.g., files of a sequence of still images or files of video images) of training patients that were exposed to stimuli known to elicit specific physiological states (e.g., stimuli from the International Affective Picture System, and/or non-visual stimuli, such as auditory stimuli, taste stimuli, smell stimuli, touch stimuli, or combinations thereof). The training data can additionally include EKG data, pneumatic respiratory data, blood pressure data, and laser Doppler data, and blood oxygenation data of the training patients.

The data received by the machine learning computer 200 can be used to build a training data set that is used to build a training feature set for the second machine learning (ML) model in the ML training module 220. In aspects, the training data set contains all data stored at a point in time in the datastore 210 by the machine learning computer 200; alternatively, the training data set contains only all the images stored in the datastore 210. Any data received by the machine learning computer 200 can be stored by the machine learning computer 200 in datastore 210, for access or retrieval when the machine learning computer 200 builds the training data set.

In step 3200, the method 3000 includes determining, by the ML training module 230 of the machine learning computer 200, a plurality of hemoglobin concentration (HC) changes based the images contained in the training data set.

In step 3300, the method 3000 includes determining, by the ML training module 230 of the machine learning computer 200, a set of bitplanes of the images in the training data set that represent the plurality of hemoglobin concentration (HC) changes in the images of the training data set. In aspects, the set of bitplanes has a high signal to noise ratio (SNR). In aspects, a set of bitplanes having a high SNR is a set of bitplanes that optimizes or maximizes signal differentiation between different physiological states under the epidermis of the body part(s) that is/are in the images. In aspects, the ML training module 230 can include a first machine learning (ML) model to determine the set of bitplanes having a red-green-blue (RGB) pixel bit-combination that maximizes the SNR. An example of a suitable first ML model that determines bitplanes can be a K-means clustering model or a Long Short Term Memory (LSTM) neural network model that can obtain an accuracy of signal differentiation and that can determine which bitplane(s) have the highest SNR. The ML training module 230 can be configured to feed the output results of the first ML model back as input into the first ML model until two successive machine learning output results have values that are within a tolerance, such as +/−5, 4, 3, 2, or 1%, of one another.

In aspects, the first ML model in the ML training module 230 can be the same ML model that is used in the vitals module 160. However, the first ML model in the ML training module 220 determines bitplanes for HC changes based on images from the training data set (images from many patients, training patients, etc.), while the ML model on the vitals module 160 determines bitplanes for the HC changes from the plurality of images captured by the smart device 100 for the specific patient. Using the same ML model in the ML training module 230 and in the vitals module 160 provides a first layer of data alignment so that the computational model that is trained in the ML training module 230 and sent to the vitals module 160 provides more accurate results for the specific patient using the smart device 100.

In step 3400, the method 3000 includes extracting spatial-temporal features from the set of bitplanes that are determined in step 3300, to create a training feature set for the second machine learning (ML) model that is trained om step 3500 to generate the computational model for use in the method 2000. In aspects, a training feature set can be created for each physiological state and a computational model can be generated for each physiological state.

In step 3500, the method 3000 includes performing the second machine learning (ML) model on the training feature set(s) created in step 3400 to generate the computational model that determines a physiological state for an input data set comprising bitplanes described herein. The output of the second ML model is the physiological state for the training feature set. In aspects, the second ML model can be a Long Short Term Memory (LSTM) neural network model or a support vector network model (e.g., utilizing nonlinear classification). In aspects, the second ML model can be performed on only a portion of the total amount of data (e.g., 70%, 80%, 90% of the training feature set), and the ML training module 220 can use the remaining data in the training feature set to validate the output of the second ML model.

In aspects, step 3500 is a training step for the second ML model, and the ML training module 230 can be configured to feed the output results of the second ML model back as input into the second ML model until two successive machine learning output results have values that are within a tolerance, such as +/−5, 4, 3, 2, or 1%, of one another.

After step 3500 is performed (with or with feedback), the second ML model can be used as the computational model that is sent to smart devices (e.g., smart device 100) as an updated version of the model used in the vitals module 160.

It should be noted that the computational model generated in method 3000 provides output for a physiological state of the training feature set that was input to the second ML model. The computational model will not output a physiological state for which it was not trained.

In aspects of the disclosure where the method 3000 is performed by the machine learning computer 200, the machine learning computer 200 can be configured to send or propagate the computational model (also referred to as the second ML model, the updated second ML model, or the updated computational model if method 3000 has already been performed to generate a previous version of the computational model) to the smart device 100 and any other smart device running the application program 150.

In aspects of the disclosure where the method 3000 is performed by the smart device 100, the vitals module 160 of the application program 150 of the smart device 100 can be configured to replace the existing computational model with the updated computational model and run the updated computational model.

Regions of Interest

In aspects of both methods 2000 and 3000, the data can be divided into regions of interest (ROIs) for a body part (e.g., nose, cheek, forehead for a face of a patient and the training patients). For different ROIs, method 3000 can be repeated to generate a computational model to determine the physiological state in each ROI. That is, the method 3000 can be performed for every ROI to generate a computational model for each ROI. It is thus contemplated that multiple computational models (e.g., each corresponding to a particular ROI of a body part) can be generated and sent to the application program 150 on the smart device 100. Subsequently, the method 2000 can be performed for each ROI to determine the physiological state in each ROI. It is believed that dividing data into ROIs can increase SNR. The physiological state for each ROI can then be compared or averaged to determine an overall physiological state.

Long Short Term (LSTM) Neural Network Model

For embodiments that utilize a LSTM neural network model, the LSTM neural network model can comprise at least three layers. The first layer is an input layer, which accepts the input data. The second layer is at least one hidden layer, where each hidden layer comprises memory cells. The final layer is an output layer that can generate the output data value based on the hidden layer(s) using a regression technique, such as logistic regression.

Each memory cell in the second layer can include an input gate, a neuron with a self-recurrent connection (a connection to itself), a forget gate, and an output gate. The self-recurrent connection can have a weight (e.g., a weight value of 1.0) so that the state of a memory cell can remain constant from one time step to another. The input gate can permit or prevent an incoming signal to alter the state of the memory cell, the output gate can permit or prevent the state of the memory cell to have an effect on other memory cells, and the forget gate can modulate the self-recurrent connection so that the memory cell remembers or forgets a previous state.

The following equations describe how a layer of memory cells is updated at every time step t, using blood flow as example. In these equations: $\vec{(x)}_t = [x_{1t}, x_{2t}, \ldots x_{nt}]$ is an input array to the memory cell layer at time t; $W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors. First, compute the values for $i_t$ (the input gate) and $\tilde{C}_t$ (the candidate value for the states of the memory cells at time t): $i_t = \sigma(W_i x_t + U_i h_t - 1 + b_i)$; and $\tilde{C}_t(W_c x_t + U_c h_{t-1} + b_f)$. Second, compute the value for $f_t$ (the activation of the forget gates at time t): $f_t = \sigma(W_f x_t + U_f h_{t-1} + b_f)$. Third, compute $C_t$ (the memory cells' new state at time t): $C_t = i_t * \tilde{C}_t + f_1 * C_{t-1}$. Fourth, compute the value of the output gates and the outputs of the output gates: $o_t = \sigma(W_o x_t + U_o h_{t-1} V_o C_t + b_o)$; and $h_t = o_t * \tan h(C_t)$. Based on the model of memory cells, for the blood flow distribution at each time step, we can calculate the output from memory cells. From an input sequence (e.g., $x_0$, $x_1$, $x_2$, . . . ), the memory cells in the hidden layer(s) will produce a representation sequence (e.g., $h_0$, $h_1$, $h_2$ . . . ).

In aspects, the representation sequence can be classified into different conditions. The output layer can generate a probability of each condition based on the representation sequence from the LSTM hidden layer(s). The vector of the probabilities at time step t can be calculated according to the following equation: $p_t = \text{softmax}(W_{output} h_t + b_{output})$, where $W_{output}$ is the weight matrix from the hidden layer to the output layer, and $b_{output}$ is the bias vector of the output layer. The condition with the maximum accumulated probability is the predicted condition of a sequence.

Figure 4:
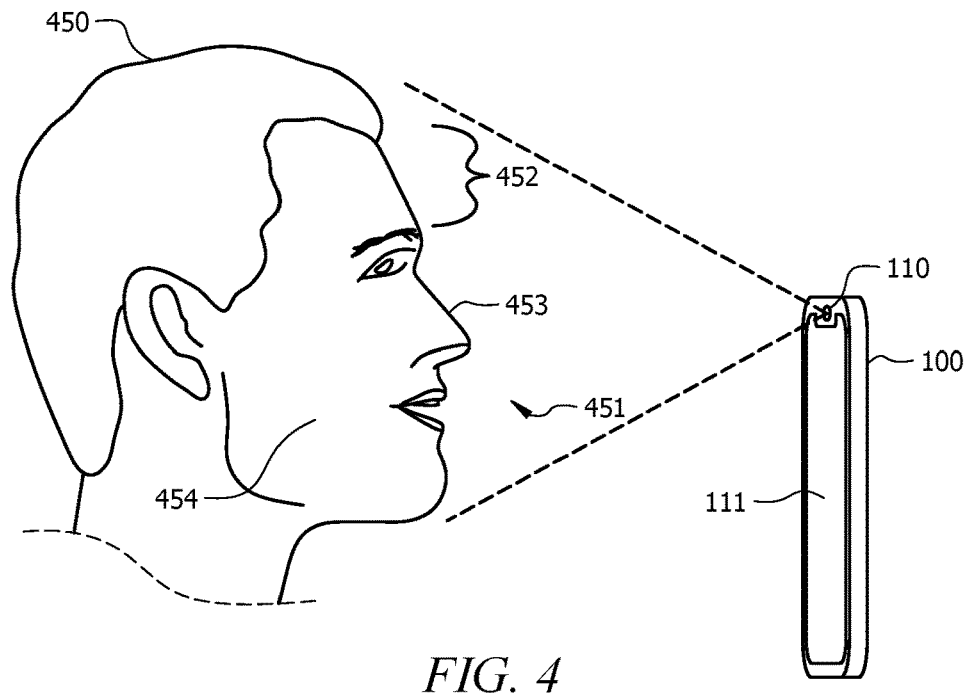
FIG. 4 illustrates a side elevational view of a camera of a smart device capturing a plurality of images of a face of patient.

FIG. 4 illustrates a side elevational view of a camera 110 of a smart device 100 capturing a plurality of images of a face 451 of patient 450. The regions of interest, e.g., the forehead 452, the nose 453, and the cheek 454 can be seen within the view of the camera 110 of the smart device 100. The smart device 100 is configured to perform the method 2000 of FIG. 2 to display a report of vital sign values and physiological state(s) associated with the vital sign values on the screen 111 of the smart device 100.

Figure 5:
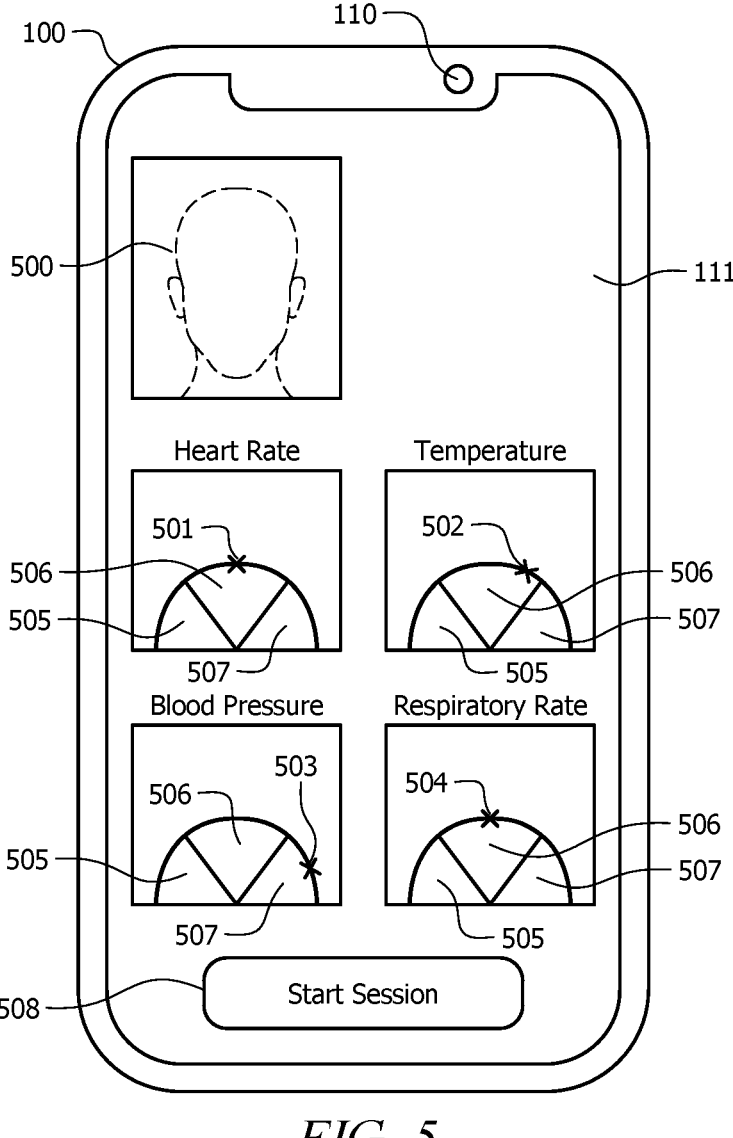
FIG. 5 illustrates a front elevational view of the smart device displaying an exemplary report.

FIG. 5 illustrates a front elevational view of the smart device 100 displaying an exemplary report. The vitals module 160 can cause the display module 130 of the smart device 100 to display the report on the screen 111 of the smart device 100. The report can include a photo 500 of the patient. The vital signs illustrated in FIG. 5 are heart rate, temperature, blood pressure, and respiration rate. The vital sign values 501, 502, 503, and 504 correspond to the vital signs of heart rate, temperature, blood pressure, and respiration rate, respectively. The physiological states in FIG. 5 are normal state 505, elevated state 506, and severe state 507. Each vital sign value 501, 502, 503, and 504 is displayed relative to the physiological states of normal state 505, elevated state 506, and severe state 507. That is vital sign value 501 for heart rate is in the elevated state 506. The vital sign value 502 for temperature is in the elevated state 506, close to the border between the elevated state 506 and the severe state 507. The vital sign value 503 for blood pressure is in the severe state 507. The vital sign value 504 for respiratory rate is in the elevated state 506.

As an example, a threshold range can be that at least one of the vital sign values 501, 502, 503, and 504 is in a severe physiological state 507. In FIG. 5, the blood pressure vital sign value 503 is in the severe state 507.

In aspects, upon determining that the blood pressure vital sign value 503 is in the sever physiological state 507, the application program 150 can be configured to display a virtual button 508 (e.g., labeled with "Start Session") on the screen 111 of the smart device 100. The patient using the smart device 100 can select the virtual button 508, and the application program 150 can activate the call module 140 or the video streaming module 170 running on the smart device 100 based on determining the physiological state for the blood pressure vital sign value 503 is outside of the threshold range, i.e., is in the severe state 507.

In aspects, upon determining that the blood pressure vital sign value 503 is in the sever physiological state 507, the application program 150 can be configured to activate the call module 140 or the video streaming module 170 running on the smart device 100 based on determining the physiological state for the blood pressure vital sign value 503 is outside of the threshold range, i.e., is in the severe state 507, without requesting patient input (e.g., no selection of the virtual button 508 is required for the application program 150 to activate the call module 140 or the video streaming module 170).

In other aspects, the threshold range can be that more than two vital sign values 501, 502, 503, and 504 is in an elevated state 506; or other combination of states 505, 506, and 507.

While the vital sign values 501, 502, 503, and 504 are illustrated as "X"s relative to a pie-type chart of physiological states, it is contemplated that the vital sign values 501, 502, 503, and 504 can be illustrated in other manners, such as in bar graph format with a color of the bar indicating the physiological state (e.g., green is normal physiological state for the vital sign value, yellow is elevated physiological state for the vital sign value, and red is severe physiological state for the vital sign value).

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:
1. A method comprising:
capturing, by camera of a smart device, a plurality of images of a body part of a patient;

determining, by the smart device, a plurality of hemoglobin concentration (HC) changes based on the plurality of images;

determining, by the smart device, a set of bitplanes of the plurality of images that represent the plurality of hemoglobin concentration (HC) changes of the patient;

extracting, by the smart device, a value for a vital sign from the plurality of HC changes;

building, by the smart device, a feature set comprising the plurality of HC changes;

performing, by the smart device, a trained machine learning model comprising a computational model on the feature set to obtain an output data set comprising a physiological state for the vital sign;

determining, by the smart device, the physiological state is outside of a threshold range; and activating, by the smart device, a call module or a video streaming module running on the smart device based on determining the physiological state is outside of the threshold range.

2. The method of claim 1, further comprising:

receiving, by the smart device from a machine learning computer, the trained machine learning model.

3. The method of claim 2, further comprising:

receiving, by the smart device from the machine learning computer, a second trained machine learning model; and performing, by the smart device, the second trained machine learning model on additional feature sets to obtain additional output data sets comprising physiological states.

4. The method of claim 1, further comprising:

generating, by the smart device, a report containing a value for the vital sign and the physiological state; and displaying, by the smart device, the report on a display of the smart device.

5. The method of claim 4, wherein the report visually characterizes the vital sign relative to the physiological state.

6. The method of claim 5, wherein the physiological state is indicated as normal, elevated, or severe in the displayed report.

7. The method of claim 1, wherein the machine learning model is trained.

8. The method of claim 1, wherein the machine learning model is a K-means clustering model or a neural network model.

9. The method of claim 1, further comprising:

receiving, by a machine learning computer from the smart device, the plurality of images;

determining, by a ML training module of the machine learning computer, a second plurality of hemoglobin concentration (HC) changes based on the plurality of images;

determining, by the ML training module of the machine learning computer, a second set of bitplanes of the plurality of images that represent the second plurality of hemoglobin concentration (HC) changes;

extracting, by the ML training module of the machine learning computer, spatial-temporal features from the second set of bitplanes;

creating, by the ML training module of the machine learning computer, a training feature set;

performing, by the ML training module of the machine learning computer, a second machine learning model on the training feature set to generate the computational model.

10. The method of claim 9, wherein an output of the second machine learning model is the physiological state.

11. A computer system comprising a smart device, wherein the smart device is configured to:

capture, by camera of the smart device, a plurality of images of a body part of a patient;

determine, by an application program running on the smart device, a plurality of hemoglobin concentration (HC) changes based on the plurality of images;

determine, by the application program, a set of bitplanes of the plurality of images that represent the plurality of hemoglobin concentration (HC) changes of the patient;

extract, by the application program, a value for a vital sign from the plurality of HC changes;

build, by the application program, a feature set comprising the plurality of HC changes;

perform, by the application program, a trained machine learning model comprising a computational model on the feature set to obtain an output data set comprising a physiological state for the vital sign;

determine, by the application program, the physiological state is outside of a threshold range; and activate, by the application program, a call module running on the smart device or a video streaming module of the application program based on determining the physiological state is outside of the threshold range.

12. The computer system of claim 11, wherein the application program of the smart device is further configured to:

receive, from a machine learning computer, the trained machine learning model.

13. The computer system of claim 12, wherein the application program of the smart device is further configured to:

receive, from the machine learning computer, a second trained machine learning model; and perform the second trained machine learning model on additional feature sets to obtain additional output data sets comprising physiological states.

14. The computer system of claim 11, wherein the application program of the smart device is further configured to:

generate a report containing a value for the vital sign and the physiological state; and display the report on a display of the smart device.

15. The computer system of claim 14, wherein the report visually characterizes the vital sign relative to the physiological state.

16. The computer system of claim 15, wherein the physiological state is indicated as normal, elevated, or severe in the displayed report.

17. The computer system of claim 11, wherein the machine learning model is trained.

18. The computer system of claim 11, wherein the machine learning model is a K-means clustering model or a neural network model.

19. The computer system of claim 11, further comprising a machine learning computer, wherein the machine learning computer is configured to:

receive, from the smart device, the plurality of images;

determine, by a ML training module of the machine learning computer, a second plurality of hemoglobin concentration (HC) changes based on the plurality of images;

determine, by the ML training module of the machine learning computer, a second set of bitplanes of the plurality of images that represent the second plurality of hemoglobin concentration (HC) changes;

extract, by the ML training module of the machine learning computer, spatial-temporal features from the second set of bitplanes;

create, by the ML training module of the machine learning computer, a training feature set based on the spatial-temporal features;

perform, by the ML training module of the machine learning computer, a second machine learning model on the training feature set to generate the computational model.

20. The computer system of claim 19, wherein an output of the second machine learning model is the physiological state.

* * * * *